US009675068B2

(12) United States Patent
Herrera et al.

(10) Patent No.: US 9,675,068 B2
(45) Date of Patent: *Jun. 13, 2017

(54) SOLID FORM SODIUM LAURYL SULFATE (SLS) CRAWLING PEST ELIMINATION COMPOSITION

(71) Applicant: ECOLAB USA INC., St. Paul, MN (US)

(72) Inventors: Kelly Herrera, South Saint Paul, MN (US); Stephen John Barcay, Burnsville, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,439

(22) Filed: Dec. 12, 2014

(65) Prior Publication Data

US 2015/0098923 A1 Apr. 9, 2015

Related U.S. Application Data

(63) Continuation of application No. 13/340,239, filed on Dec. 29, 2011, now abandoned, which is a continuation of application No. 12/477,640, filed on Jun. 3, 2009, now Pat. No. 8,110,608.

(60) Provisional application No. 61/059,168, filed on Jun. 5, 2008.

(51) Int. Cl.
  *A01N 41/02* (2006.01)
(52) U.S. Cl.
  CPC .................................. *A01N 41/02* (2013.01)
(58) Field of Classification Search
  None
  See application file for complete search history.

(56) References Cited

U.S. PATENT DOCUMENTS

| 3,274,052 A | 9/1966 | Yaffe |
| 3,808,339 A | 4/1974 | Bordenca |
| 3,873,725 A | 3/1975 | Skinner et al. |
| 3,920,442 A | 11/1975 | Albert et al. |
| 4,181,734 A | 1/1980 | D'Silva |
| 4,191,773 A | 3/1980 | Dorn |
| 4,194,001 A | 3/1980 | Ruscoe et al. |
| 4,195,080 A | 3/1980 | Herrera et al. |
| 4,198,397 A | 4/1980 | Gillings et al. |
| 4,198,782 A | 4/1980 | Kydonieus et al. |
| 4,200,644 A | 4/1980 | Engel |
| 4,206,230 A | 6/1980 | Paul |
| 4,215,138 A | 7/1980 | Ozawa et al. |
| 4,218,468 A | 8/1980 | Paul |
| 4,226,881 A | 10/1980 | Barer |
| 4,235,872 A | 11/1980 | Tocker |
| 4,235,927 A | 11/1980 | Engel |
| 4,237,168 A | 12/1980 | Reifschneider |
| 4,243,677 A | 1/1981 | Engel |
| 4,255,435 A | 3/1981 | Watkins et al. |
| 4,263,287 A | 4/1981 | Dennis |
| 4,264,606 A | 4/1981 | Ozawa et al. |
| 4,265,906 A | 5/1981 | Kasamatsu et al. |
| 4,265,907 A | 5/1981 | Paul |
| 4,268,520 A | 5/1981 | Grantham |
| 4,268,521 A | 5/1981 | Knabke |
| 4,268,525 A | 5/1981 | Paul |
| 4,271,181 A | 6/1981 | Eastburg |
| 4,279,895 A | 7/1981 | Carle |
| 4,291,055 A | 9/1981 | Chen |
| 4,291,058 A | 9/1981 | Suchy |
| 4,299,258 A | 11/1981 | Brite |
| 4,303,640 A | 12/1981 | Fuyama et al. |
| 4,308,279 A | 12/1981 | Smeltz |
| 4,313,941 A | 2/1982 | Duinker et al. |
| 4,320,139 A | 3/1982 | Takei et al. |
| 4,320,140 A | 3/1982 | Crounse et al. |
| 4,335,118 A | 6/1982 | Fischer et al. |
| 4,335,252 A | 6/1982 | Engel |
| 4,342,778 A | 8/1982 | Drabek et al. |
| 4,346,091 A | 8/1982 | Sanborn |
| 4,346,092 A | 8/1982 | Sanborn |
| 4,357,348 A | 11/1982 | Kasamatsu et al. |

(Continued)

FOREIGN PATENT DOCUMENTS

| CN | 101326918 | 12/2008 |
| EP | 0 008 880 A1 | 3/1980 |

(Continued)

OTHER PUBLICATIONS

Stepanol Needle—form SDS Product Bulletin, Jan. 2008.*
Scrinivas et al., J Dispersion Sci Tech 28: 477-484 (2007).*
Jakasa, I. et al., "Increased permeability for polyethylene glycols through skin compromised by sodium lauryl sulphate," Experimental Dermatology, vol. 15, pp. 801-807 (2006).
Longman, G.F., "The analysis of detergents," Talanta, vol. 22, pp. 621-636 (1975).
Sinniah, B., "Insecticidal effect of aliphatic alcohols against aquatic stages of Aedes mosquitoes," Transactions of the Royal Society of Tropical Medicine and Hygiene, vol. 77, No. 1, pp. 35-38 (1983).
Sodium Lauryl Sulfate; Exemption From the Requirement of a Tolerance, Federal Register, vol. 74, No. 154, pp. 40503-40509 (Aug. 12, 2009).

(Continued)

*Primary Examiner* — Sue Liu
*Assistant Examiner* — Thor Nielsen
(74) *Attorney, Agent, or Firm* — Merchant & Gould P.C.

(57) ABSTRACT

A composition and method of eliminating pests combines water and a solid form of sodium lauryl sulfate to form a pesticide composition effective to cause mortality in pests. The composition is applied to the indoor structure in an area which the pests inhabit. The sodium lauryl sulfate can be in needle form, pellet form or powder form and constitutes between about 1% and about 10% by weight of the pesticide composition. The composition may be applied to an area inhabited by cockroaches, including, but not limited to, in crevices, cracks, corners, wall and floor junctures or other enclosed or partially enclosed areas of a structure.

17 Claims, No Drawings

(56) References Cited

U.S. PATENT DOCUMENTS

| | | |
|---|---|---|
| 4,359,580 A | 11/1982 | Grasso |
| 4,361,554 A | 11/1982 | Saunders |
| 4,370,346 A | 1/1983 | Punja |
| 4,375,476 A | 3/1983 | Cardis |
| 4,376,785 A | 3/1983 | Matsuo et al. |
| 4,380,537 A | 4/1983 | Monroe |
| 4,382,927 A | 5/1983 | Sherman |
| 4,386,071 A | 5/1983 | Carle |
| 4,391,820 A | 7/1983 | Holan et al. |
| 4,391,823 A | 7/1983 | Boxler et al. |
| 4,393,074 A | 7/1983 | Middleton |
| 4,399,152 A | 8/1983 | Brouwer et al. |
| 4,405,353 A | 9/1983 | Angyan et al. |
| 4,415,748 A | 11/1983 | Scharpf et al. |
| 4,419,350 A | 12/1983 | Letchworth et al. |
| 4,423,028 A | 12/1983 | Walker et al. |
| 4,423,042 A | 12/1983 | Dorn et al. |
| 4,426,379 A | 1/1984 | Edwards |
| 4,436,719 A | 3/1984 | Lindaberry |
| 4,438,137 A | 3/1984 | Allan |
| 4,439,430 A | 3/1984 | Reifschneider |
| 4,447,413 A | 5/1984 | Rippstein, Jr. |
| 4,450,169 A | 5/1984 | Nezot et al. |
| 4,457,923 A | 7/1984 | Fahmy |
| 4,461,758 A | 7/1984 | Brite |
| 4,461,764 A | 7/1984 | Magee |
| 4,470,966 A | 9/1984 | Costanza et al. |
| 4,481,215 A | 11/1984 | Tocker |
| 4,490,380 A | 12/1984 | Redemann |
| 4,490,390 A | 12/1984 | Priester et al. |
| 4,496,586 A | 1/1985 | Matsui et al. |
| 4,501,742 A | 2/1985 | Harris |
| 4,504,483 A | 3/1985 | Ozawa et al. |
| 4,510,133 A | 4/1985 | Evans |
| 4,518,593 A | 5/1985 | Juvin et al. |
| 4,536,506 A | 8/1985 | Marcoux et al. |
| 4,540,710 A | 9/1985 | Holan et al. |
| 4,551,546 A | 11/1985 | Punja |
| 4,562,062 A | 12/1985 | Shinjo et al. |
| 4,564,631 A | 1/1986 | Elbert et al. |
| 4,564,639 A | 1/1986 | Nagase et al. |
| 4,567,199 A | 1/1986 | Crowley |
| 4,568,541 A | 2/1986 | Dorn et al. |
| 4,568,670 A | 2/1986 | Reifschneider et al. |
| 4,582,825 A | 4/1986 | Baumann et al. |
| 4,595,679 A | 6/1986 | Broadbent |
| 4,596,890 A | 6/1986 | Kisida et al. |
| 4,596,892 A | 6/1986 | Plummer |
| 4,602,945 A | 7/1986 | Graber et al. |
| 4,604,971 A | 8/1986 | Baker et al. |
| 4,617,316 A | 10/1986 | Plummer |
| 4,632,936 A | 12/1986 | Boase et al. |
| 4,636,523 A | 1/1987 | Plummer |
| 4,650,792 A | 3/1987 | Underwood |
| 4,659,703 A | 4/1987 | Chavdarian |
| 4,662,103 A | 5/1987 | Cheng |
| 4,666,747 A | 5/1987 | Quinn |
| 4,680,294 A | 7/1987 | Shiokawa et al. |
| 4,685,423 A | 8/1987 | Baker et al. |
| 4,688,349 A | 8/1987 | Renth |
| 4,696,822 A | 9/1987 | Matsumura et al. |
| 4,709,068 A | 11/1987 | Sieburth |
| 4,725,589 A | 2/1988 | Tsuboi et al. |
| 4,737,509 A | 4/1988 | Plummer |
| 4,767,773 A | 8/1988 | Ayad |
| 4,780,457 A | 10/1988 | Tsuboi et al. |
| 4,786,650 A | 11/1988 | Drabek |
| 4,796,381 A | 1/1989 | Kauth et al. |
| 4,798,839 A | 1/1989 | Ayad |
| 4,803,956 A | 2/1989 | Corrigan et al. |
| 4,805,341 A | 2/1989 | Maeda |
| 4,808,762 A | 2/1989 | Meier et al. |
| 4,818,525 A | 4/1989 | Kamada |
| 4,822,613 A | 4/1989 | Rodero |
| 4,826,682 A | 5/1989 | Sakharova |
| 4,833,159 A | 5/1989 | Bushell et al. |
| 4,837,209 A | 6/1989 | Chavdarian |
| 4,851,438 A | 7/1989 | Flashinski |
| 4,860,488 A | 8/1989 | Shigetoyo |
| 4,861,762 A | 8/1989 | Puritch et al. |
| 4,863,718 A | 9/1989 | Bernardo |
| 4,867,972 A | 9/1989 | Girardeau et al. |
| 4,868,209 A | 9/1989 | Punja |
| 4,873,264 A | 10/1989 | Chou et al. |
| 4,879,117 A | 11/1989 | Rombi |
| 4,888,174 A | 12/1989 | Farquharson et al. |
| 4,888,340 A | 12/1989 | Neh et al. |
| 4,889,719 A | 12/1989 | Ohtsubo et al. |
| 4,889,872 A | 12/1989 | Naumann et al. |
| 4,892,732 A | 1/1990 | Parconagian et al. |
| 4,895,871 A | 1/1990 | Lutomski et al. |
| 4,900,758 A | 2/1990 | Fisher |
| 4,904,464 A | 2/1990 | Albanese |
| 4,904,696 A | 2/1990 | Sakamoto et al. |
| 4,911,913 A | 3/1990 | Hostetter et al. |
| 4,913,893 A * | 4/1990 | Varco .................. A61K 8/046 424/47 |
| 4,925,657 A | 5/1990 | Den Braber et al. |
| 4,933,181 A | 6/1990 | Brown et al. |
| 4,936,901 A | 6/1990 | Surgant, Sr. et al. |
| 4,944,950 A | 7/1990 | Sakharova |
| 4,945,088 A | 7/1990 | Okamoto et al. |
| 4,945,107 A | 7/1990 | Minetti |
| 4,956,353 A | 9/1990 | Dowd |
| 4,963,584 A | 10/1990 | Hidasi et al. |
| 4,975,425 A | 12/1990 | Barnett, Jr. |
| 4,975,451 A | 12/1990 | Cullen et al. |
| 4,980,373 A | 12/1990 | Kisida et al. |
| 4,983,391 A | 1/1991 | Muneyuki et al. |
| 4,988,516 A | 1/1991 | Herring |
| 4,992,275 A | 2/1991 | Lush |
| 4,997,592 A | 3/1991 | Woogerd |
| 5,017,615 A | 5/1991 | Workman |
| 5,026,727 A | 6/1991 | Bushnell |
| 5,034,404 A | 7/1991 | Uneme et al. |
| 5,049,585 A | 9/1991 | Robson et al. |
| 5,061,489 A | 10/1991 | Bernier et al. |
| 5,068,229 A | 11/1991 | Benoit et al. |
| 5,091,416 A | 2/1992 | Bushell |
| 5,100,667 A | 3/1992 | Chan et al. |
| 5,106,872 A | 4/1992 | Alder et al. |
| 5,110,594 A | 5/1992 | Morita |
| 5,122,364 A | 6/1992 | Portas |
| 5,122,518 A | 6/1992 | Vrba |
| 5,128,329 A | 7/1992 | Minagawa et al. |
| 5,152,096 A | 10/1992 | Rudolph |
| 5,153,182 A | 10/1992 | Tozzi |
| 5,166,425 A | 11/1992 | Tsushima et al. |
| 5,223,270 A | 6/1993 | Jones |
| 5,225,443 A | 7/1993 | Murphy et al. |
| 5,238,949 A | 8/1993 | Shiokawa et al. |
| 5,250,575 A | 10/1993 | Wilson et al. |
| 5,262,323 A | 11/1993 | Baird et al. |
| 5,266,324 A | 11/1993 | Stendel et al. |
| 5,300,503 A | 4/1994 | Peake et al. |
| 5,320,855 A | 6/1994 | Roche et al. |
| 5,326,560 A | 7/1994 | Henderson |
| 5,338,544 A | 8/1994 | Donovan |
| 5,352,674 A | 10/1994 | Cummings |
| 5,369,027 A | 11/1994 | Lambert et al. |
| 5,389,662 A | 2/1995 | Pap et al. |
| 5,401,771 A | 3/1995 | Demassey et al. |
| 5,427,794 A | 6/1995 | Miles |
| 5,446,019 A | 8/1995 | Ely et al. |
| 5,455,256 A | 10/1995 | Kamochi et al. |
| 5,457,178 A | 10/1995 | Jackson et al. |
| 5,476,869 A | 12/1995 | Murai et al. |
| 5,510,363 A | 4/1996 | Thirugnanam |
| 5,516,747 A | 5/1996 | Lachut |
| 5,521,192 A | 5/1996 | Henrie, II et al. |
| 5,531,981 A | 7/1996 | Kuwazuru et al. |
| 5,571,829 A | 11/1996 | Thirugnanam |
| 5,578,250 A | 11/1996 | Thomas et al. |
| 5,595,749 A | 1/1997 | Rascher et al. |

(56) References Cited

U.S. PATENT DOCUMENTS

| | | |
|---|---|---|
| 5,614,558 A | 3/1997 | James et al. |
| 5,620,678 A | 4/1997 | Burke |
| 5,631,276 A | 5/1997 | Kern |
| 5,641,499 A | 6/1997 | Bencsits |
| 5,646,133 A | 7/1997 | Sanders |
| 5,663,117 A | 9/1997 | Warner |
| 5,674,846 A | 10/1997 | Johnson et al. |
| 5,676,959 A | 10/1997 | Heitz et al. |
| 5,683,971 A | 11/1997 | Rose et al. |
| 5,702,703 A | 12/1997 | Schnepf et al. |
| 5,705,193 A | 1/1998 | Bourgogne et al. |
| 5,709,890 A | 1/1998 | Sanders et al. |
| 5,712,281 A | 1/1998 | Cullen et al. |
| 5,712,295 A | 1/1998 | Mencke et al. |
| 5,756,459 A | 5/1998 | Jackson et al. |
| 5,773,016 A | 6/1998 | Nelson |
| 5,783,203 A | 7/1998 | Schütte et al. |
| 5,792,755 A | 8/1998 | Sagenmüller et al. |
| 5,849,870 A | 12/1998 | Warren et al. |
| 5,860,266 A | 1/1999 | Martinet et al. |
| 5,885,598 A | 3/1999 | Knauf et al. |
| 5,888,989 A | 3/1999 | Kern |
| 5,910,323 A | 6/1999 | Lajoie et al. |
| 5,925,670 A | 7/1999 | Silverman et al. |
| 5,935,943 A | 8/1999 | Asai et al. |
| 5,939,438 A | 8/1999 | Yeager et al. |
| 5,942,542 A | 8/1999 | Killick et al. |
| 5,945,114 A | 8/1999 | Ogawa et al. |
| 5,977,186 A | 11/1999 | Franklin |
| 5,994,331 A | 11/1999 | Erdelen et al. |
| 5,998,330 A | 12/1999 | Felton |
| 5,998,475 A | 12/1999 | James et al. |
| 5,998,484 A | 12/1999 | Zobitne et al. |
| 6,022,881 A | 2/2000 | Asai et al. |
| 6,060,489 A | 5/2000 | Erdelen et al. |
| 6,074,656 A | 6/2000 | Katsuda et al. |
| 6,077,860 A | 6/2000 | Meunier et al. |
| 6,090,398 A | 7/2000 | Schroder et al. |
| 6,093,413 A | 7/2000 | Matson |
| 6,103,763 A | 8/2000 | Horst |
| 6,110,866 A | 8/2000 | Walker |
| 6,153,181 A | 11/2000 | Nelson et al. |
| 6,162,825 A | 12/2000 | Silverman et al. |
| 6,218,407 B1 | 4/2001 | Erdelen et al. |
| 6,258,369 B1 | 7/2001 | Pullen |
| 6,265,384 B1 * | 7/2001 | Pearlman ............ A01N 31/02 132/142 |
| 6,277,389 B1 | 8/2001 | Pullen |
| 6,296,865 B1 | 10/2001 | Dujardin et al. |
| 6,429,180 B1 | 8/2002 | Wisniewski et al. |
| 6,444,690 B2 | 9/2002 | Erdelen et al. |
| 6,482,863 B2 | 11/2002 | Munagavalasa et al. |
| 6,492,357 B1 | 12/2002 | Nakakura et al. |
| 6,531,163 B1 | 3/2003 | Bessette |
| 6,534,529 B2 | 3/2003 | Uhr et al. |
| 6,541,448 B2 | 4/2003 | Isaac et al. |
| 6,544,538 B1 | 4/2003 | Caine |
| 6,548,085 B1 | 4/2003 | Zobitne et al. |
| 6,564,502 B2 | 5/2003 | Barcay et al. |
| 6,576,661 B1 | 6/2003 | Brück et al. |
| 6,582,712 B2 | 6/2003 | Pullen |
| 6,582,732 B1 | 6/2003 | Bender et al. |
| 6,585,990 B1 | 7/2003 | Huang |
| 6,588,374 B1 | 7/2003 | Cottrell et al. |
| 6,593,293 B1 | 7/2003 | Baum et al. |
| 6,596,271 B2 | 7/2003 | Hammock et al. |
| 6,662,491 B2 | 12/2003 | Flinn et al. |
| 6,814,030 B2 | 11/2004 | Cottrell et al. |
| 6,849,633 B2 | 2/2005 | Okui et al. |
| 6,855,330 B2 | 2/2005 | Sirinyan et al. |
| 6,855,348 B2 | 2/2005 | Ahn et al. |
| 6,867,223 B2 | 3/2005 | Cottrell et al. |
| 6,900,190 B2 | 5/2005 | Fischer et al. |
| 6,919,090 B2 | 7/2005 | Fischer et al. |
| 6,984,662 B2 | 1/2006 | Cottrell et al. |
| 6,986,898 B1 | 1/2006 | Bessette |
| 7,019,036 B2 | 3/2006 | Hiromoto |
| 7,084,138 B2 | 8/2006 | Fischer et al. |
| 7,091,233 B2 | 8/2006 | Fischer et al. |
| 7,125,565 B2 | 10/2006 | Sugishita et al. |
| 7,132,448 B2 | 11/2006 | Cottrell et al. |
| 7,192,600 B2 | 3/2007 | Barcay et al. |
| 7,201,926 B2 | 4/2007 | Fried et al. |
| 7,205,289 B2 | 4/2007 | Fischer et al. |
| 7,208,474 B2 | 4/2007 | Bermudez et al. |
| 7,214,788 B2 | 5/2007 | Guzov et al. |
| 7,232,845 B2 | 6/2007 | Fischer et al. |
| 7,247,756 B2 | 7/2007 | Theodoridis et al. |
| 7,282,492 B2 | 10/2007 | Wengel et al. |
| 7,288,572 B2 | 10/2007 | Konze et al. |
| 7,297,351 B2 | 11/2007 | Hiromoto |
| 7,312,204 B2 | 12/2007 | Erdelen et al. |
| 7,326,704 B2 | 2/2008 | Selby |
| 7,341,735 B2 | 3/2008 | Pullen |
| 7,341,736 B2 | 3/2008 | Flashinski |
| 7,345,092 B2 | 3/2008 | Cottrell et al. |
| 7,354,595 B2 | 4/2008 | Cottrell et al. |
| 7,371,768 B2 | 5/2008 | Okui et al. |
| 7,384,647 B2 | 6/2008 | Ferko, IV |
| 7,384,927 B2 | 6/2008 | Iori |
| 7,416,880 B2 | 8/2008 | Park et al. |
| 7,423,062 B2 | 9/2008 | Tsushima |
| 7,435,411 B2 | 10/2008 | Park et al. |
| 7,439,280 B2 | 10/2008 | Lu et al. |
| 8,110,608 B2 | 2/2012 | Herrera et al. |
| 8,877,219 B2 | 11/2014 | Bessette |
| 8,968,757 B2 | 3/2015 | Man et al. |
| 2001/0014654 A1 | 8/2001 | Davister et al. |
| 2003/0073667 A1 | 4/2003 | Endris et al. |
| 2003/0092710 A1 | 5/2003 | Nakakura et al. |
| 2003/0152603 A1 | 8/2003 | Johnson |
| 2003/0170341 A1 | 9/2003 | Goodman et al. |
| 2004/0175405 A1 | 9/2004 | Mohamed Mahgoub et al. |
| 2005/0003001 A1 | 1/2005 | Yamaguchi et al. |
| 2005/0038094 A1 | 2/2005 | Warrington |
| 2005/0058681 A1 | 3/2005 | Johnson |
| 2005/0112165 A1 | 5/2005 | Taylor |
| 2005/0152937 A1 | 7/2005 | Lin |
| 2005/0169954 A1 | 8/2005 | Cottrell et al. |
| 2005/0196416 A1 | 9/2005 | Kipp et al. |
| 2005/0233986 A1 | 10/2005 | Clough |
| 2005/0244387 A1 | 11/2005 | Grewal |
| 2005/0244445 A1 | 11/2005 | Anderson |
| 2005/0266036 A1 | 12/2005 | Awada et al. |
| 2006/0034898 A1 | 2/2006 | Amodt et al. |
| 2006/0063829 A1 | 3/2006 | Andersch et al. |
| 2006/0083764 A1 | 4/2006 | Hernandez et al. |
| 2006/0093637 A1 | 5/2006 | Stock et al. |
| 2006/0115506 A1 | 6/2006 | Harmer et al. |
| 2006/0135564 A1 | 6/2006 | Kim et al. |
| 2006/0257440 A1 | 11/2006 | Asai et al. |
| 2007/0003586 A1 | 1/2007 | Homoelle, Jr. et al. |
| 2007/0009563 A1 | 1/2007 | Hataipitisuk |
| 2007/0048346 A1 | 3/2007 | Ido |
| 2007/0065476 A1 * | 3/2007 | Sexton ............... A01N 25/006 424/410 |
| 2007/0071785 A1 | 3/2007 | Craven et al. |
| 2007/0178128 A1 | 8/2007 | Bessette |
| 2007/0202089 A1 | 8/2007 | Bermudez et al. |
| 2007/0254927 A1 | 11/2007 | Cottrell et al. |
| 2007/0254951 A1 | 11/2007 | Cottrell et al. |
| 2007/0259015 A1 | 11/2007 | Patterson et al. |
| 2007/0264297 A1 | 11/2007 | Scialdone et al. |
| 2007/0275971 A1 | 11/2007 | Erdelen et al. |
| 2007/0276014 A1 | 11/2007 | Cottrell et al. |
| 2008/0003185 A1 | 1/2008 | Valpey et al. |
| 2008/0038214 A1 | 2/2008 | Cottrell et al. |
| 2008/0038383 A1 | 2/2008 | Bessette et al. |
| 2008/0064603 A1 | 3/2008 | Pullen |
| 2008/0070787 A1 | 3/2008 | Pullen |
| 2008/0112992 A1 | 5/2008 | Mohamed Mahgoub et al. |
| 2008/0118461 A1 | 5/2008 | Boucher, Jr. et al. |
| 2008/0214400 A1 | 9/2008 | Pullen |
| 2008/0214502 A1 | 9/2008 | Smogoleski et al. |

(56) References Cited

U.S. PATENT DOCUMENTS

| | | |
|---|---|---|
| 2008/0214634 A1 | 9/2008 | Konze et al. |
| 2008/0233159 A1 | 9/2008 | Katsuda et al. |
| 2008/0257075 A1 | 10/2008 | Ropiak |
| 2008/0300225 A1 | 12/2008 | Marrone |
| 2009/0057442 A1 | 3/2009 | Nguyen |
| 2009/0082204 A1 | 3/2009 | Royalty et al. |
| 2010/0227010 A1 | 9/2010 | Jones |
| 2011/0054026 A1* | 3/2011 | Doyle ............... A01N 31/16 514/558 |
| 2012/0087964 A1 | 4/2012 | Man et al. |
| 2012/0087987 A1 | 4/2012 | Man et al. |
| 2012/0088828 A1 | 4/2012 | Man et al. |
| 2015/0140056 A1 | 5/2015 | Man et al. |

FOREIGN PATENT DOCUMENTS

| | | |
|---|---|---|
| EP | 0008880 | 3/1980 |
| EP | 0 582 065 A1 | 2/1994 |
| EP | 0 936 859 B1 | 8/2002 |
| EP | 1 158 964 B1 | 4/2004 |
| EP | 1 490 025 B1 | 2/2008 |
| GB | 1 572 357 A | 7/1980 |
| GB | 1572357 | 7/1980 |
| GB | 1 604 860 A | 12/1981 |
| GB | 1604860 | 12/1981 |
| GB | 2 144 994 A | 3/1985 |
| GB | 2 145 086 A | 3/1985 |
| GB | 2144994 | 3/1985 |
| GB | 2145086 | 3/1985 |
| GB | 2 150 565 A | 7/1985 |
| WO | 93/22915 | 11/1993 |
| WO | WO 93/22915 A1 | 11/1993 |
| WO | WO 94/22311 | 10/1994 |
| WO | WO 97/02748 | 1/1997 |
| WO | WO 01/95726 A1 | 12/2001 |
| WO | WO 2008/032328 A2 | 3/2008 |
| WO | WO 2009/147648 A2 | 12/2009 |
| WO | WO2010037503 | 4/2010 |

OTHER PUBLICATIONS van der Merwe, D. et al., "Effect of vehicles and sodium lauryl sulphate on xenobiotic permeability and stratum corneum partitioning in porcine skin," Toxicology, vol. 206, pp. 325-335 (2005).

Wadaan, M. et al., "Skin Lesions Induced by Sodium Lauryl Sulfate (SLS) in Rabbits," J. Med. Sci., vol. 5, No. 4, pp. 320-323 (Oct.-Dec. 2005).

International Search Report and Written Opinion cited in International Application No. PCT/US2011/055999 mailed May 18, 2012.

Merck Index, entry 8392, for sodium lauryl sulfate, Martha Windholz, Editor (1976), p. 1116.

Wege, P. J., et al. "A microencapsulated formulation of lambda-cyhalothrin." Proceedings of the 3rd international conference on urban pests. 1999.

EcoEXEMP IC2, "Insecticide Concentrate" Copyright 2005 EcoSMART Technologies, Inc., p. 1-2.

Healthy-Communications, "Sodium Lauryl Sulfate and Sodium Laureth Sulfate," <http://healthy-communications.com/slsmostdangerousirritant.html>, published Feb. 7, 2009, p. 1-2.

Agilent Technologies, Inc., "Fatty alcohol, C20-C28, Analysis of Fatty Alcohol in Olive Oil," (2011).

* cited by examiner

SOLID FORM SODIUM LAURYL SULFATE (SLS) CRAWLING PEST ELIMINATION COMPOSITION

CROSS REFERENCE TO RELATED APPLICATIONS

This application is a continuation of U.S. application Ser. No. 13/340,239, filed Dec. 29, 2011 which is a continuation of U.S. application Ser. No. 12/477,640, filed Jun. 3, 2009, both entitled "Solid Form Sodium Lauryl Sulfate (SLS) Pesticide Composition," issued as U.S. Pat. No. 8,110,608, which claims the benefit under 35 U.S.C. §119 of U.S. Provisional Application No. 61/059,168, filed on Jun. 5, 2008, entitled "Solid Form Sodium Lauryl Sulfate (SLS) Pesticide Composition," both of which are herein incorporated by reference in their entirety.

TECHNICAL FIELD

The present invention relates generally to the field of pesticides. In particular, the present invention relates to using a solid form of sodium lauryl sulfate (SLS) in a pesticide composition. The present invention also relates to methods of using the pesticide composition.

BACKGROUND

Left unattended, pests such as insects and rodents can quickly infest enclosed structures, such as restaurants and homes. Examples of crawling pests which can infest areas in and around enclosed structures include, for example, cockroaches, ants, ground beetles and spiders. In addition to being a nuisance, some of these pests can also bring pathogens into the restaurant or home, creating unsanitary eating and living conditions.

The use of pesticide compositions has aided in decreasing the infestation of insects in and around residential and commercial structures. Various types of pesticide compositions and methods of repelling or terminating crawling pests are currently available, including gel baits, glue pads and poisons. Because the pests can enter walls through small cracks and crevices and inhabit relatively inaccessible areas, such as within floors and behind walls, various tools can be used to "flush" the pests from the wall. For example, flushing agents can be sprayed into the areas to irritate or agitate the pests and cause them to leave the inaccessible areas and come out into the open and expose themselves. Once the pests enter the open environment, they are exposed to a pesticide composition that terminates them.

In more recent years, attention has been directed to producing pesticides that are effective and ecologically friendly. In line with this trend, the Environmental Protection Agency (EPA) has issued a list of minimum risk pesticides §25(b) of the Federal Insecticide, Fungicide, and Rodenticide Act (FIFRA) that are not subject to federal registration requirements because their active and inert ingredients are demonstrably safe for their intended use. There is an ongoing need to provide effective pesticides which have reduced environmental impact.

SUMMARY

One embodiment of the present invention is a method of eliminating cockroaches by mixing water and solid form sodium lauryl sulfate to form a pesticide composition effective to cause mortality in cockroaches, wherein the sodium lauryl sulfate constitutes between about 1% and about 10% by weight of the pesticide composition, and applying the pesticide composition to an enclosed or partially enclosed area in a structure inhabited by cockroaches. The pesticide composition may be applied to an area inhabited by cockroaches, including, but not limited to, in crevices, cracks, corners, wall and floor junctures or other enclosed or partially enclosed areas of the indoor structure.

Another embodiment of the present invention is a composition produced by the method of combining water and solid form sodium lauryl sulfate to form a solution effective to cause mortality in pests. The concentration of sodium lauryl sulfate may be less than about 10% by weight of the composition, more particularly between about 1% and about 6% by weight of the composition. The composition according to certain embodiments may include only water and sodium lauryl sulfate, essentially only water and sodium lauryl sulfate, or may be free or substantially free of non-food grade components and/or components that are not ecologically safe. In other embodiments, the composition may include a pesticide, and in other embodiments the composition by include a pesticide in an amount less than 0.5% by weight.

DETAILED DESCRIPTION

The pesticide composition of the present invention may be employed at any of a wide variety of locations in which it is desired to eliminate pest infestation. The pesticide composition is effective in killing crawling pests, and in particular cockroaches. In addition, the pesticide composition is generally more ecologically sustainable than traditional pesticides, making it particularly useful where it is desired to use an environmentally friendly pesticide. Such applications include using the pesticide composition in and around restaurants, stores, homes, or other generally enclosed structures in which humans and animals are present. While the pesticide composition is discussed as being used to eliminate cockroaches, the pesticide composition may be used to eliminate any crawling pests, such as, for example, ants, ground beetles, spiders and the like. In addition, while the pesticide composition is discussed as being applied to and around partially enclosed or enclosed areas, the pesticide composition may also be used in an agricultural environment.

The pesticide compositions may include concentrate compositions or may be diluted to form use compositions. In general, a concentrate refers to a composition that is intended to be diluted with water to provide a use solution that contacts an object to provide the desired effect. The pesticide composition that contacts the pests or surrounding areas can be referred to as the use composition. The use solution can include additional functional ingredients. The use composition can have a solids content that is sufficient to provide the desired level of efficacy while avoiding wasting the pesticide composition. The solids concentration refers to the concentration of the non-water components in the use composition.

In one embodiment, the pesticide composition of the present invention includes a combination of sodium lauryl sulfate (SLS) and water. In particular, the pesticide composition includes a combination of a solid form of sodium lauryl sulfate and water. Suitable component concentrations for a concentrate of the pesticide composition include between about 90% and about 100% sodium lauryl sulfate by weight and balance water, particularly between about 93% and about 100% sodium lauryl sulfate by weight and balance water and more particularly between about 95% and about 100% sodium lauryl sulfate by weight and balance water. Suitable component concentrations for a use solution of the pesticide composition include between about 1% and about 10% sodium lauryl sulfate by weight and balance water and particularly between about 1% and about 6% sodium lauryl sulfate by weight and balance water. At concentrations higher than about 12% by weight sodium lauryl sulfate, solid form sodium lauryl sulfate may not effectively form a solution. In other embodiments, similar intermediate concentrate and use concentrations may also be present in the cleaning compositions of the invention.

Examples of suitable solid forms of sodium lauryl sulfate include, but are not limited to, powder, pellet and block forms. An example of a particularly suitable pellet form of sodium lauryl sulfate is needle form sodium lauryl sulfate. An example of a suitable commercially available needle form sodium lauryl sulfate includes Stepanol DX®, CAS number 151-21-3, available from Stephan Company, Northfield, Ill. While both powder form and pellet form sodium lauryl sulfate may be used to form the pesticide composition of the present invention, pellet form sodium lauryl sulfate is generally easier to handle and does not become airborne as easily as other solid forms.

When liquid concentrate form sodium lauryl sulfate is used, suitable component concentrations for the pesticide composition include between about 1% and about 18% sodium lauryl sulfate by volume and balance water and particularly between about 6% and about 18% sodium lauryl sulfate by volume and balance water. While the liquid concentrate form of sodium lauryl sulfate may also be effective in eliminating pests, liquid concentrate sodium lauryl sulfate has a freezing point of about 53 degrees Fahrenheit, making liquid concentrate sodium lauryl sulfate difficult to use effectively in certain applications.

Because sodium lauryl sulfate is on the §25(b) exempt list of minimum risk pesticides published by the EPA in the FIFRA, the pesticide composition of the present invention is not only ecologically acceptable but is also a food grade material. In one embodiment, the pesticide composition includes an effective amount of sodium lauryl sulfate and water. In another embodiment, the pesticide composition further includes additional components that are on the list of minimum risk pesticides and/or materials that are otherwise considered ecologically safe, non-toxic or food grade. For example, in one embodiment, the pesticide composition does not include components which may be considered toxic or carcinogenic when exposed to humans. In a further embodiment, the pesticide composition contains conventional pesticides or other components in concentrations of less than about 0.5% by weight of a use solution of the pesticide composition, particularly less than about 0.1% by weight of a use solution of the pesticide composition and more particularly less than about 0.01% by weight of a use solution of the pesticide composition. In yet another embodiment, the pesticide composition includes conventional pesticides at lower concentrations than typically required when used as the primary pesticide due to the presence of the sodium lauryl sulfate.

Additional Functional Ingredients

In a further embodiment, the pesticide composition may also include additional components or agents, such as additional functional ingredients. As such, in some embodiments, the pesticide composition including sodium lauryl sulfate and water may provide a large amount, or even all of the total weight of the pesticide composition, for example, in embodiments having few or no additional functional materials disposed therein. The functional materials provide desired properties and functionalities to the pesticide composition. For the purpose of this application, the term "functional materials" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and a broad variety of other functional materials may be used.

The pesticide composition of the present invention may include attractants such as cockroach pheromones (e.g., sex attractants, aggregation pheromones) or food-based attractants (e.g., methylcyclopentenalone, maltol, fenugreek and other flavorings). When an attractant is included in the pesticide composition, the attractant may constitute between about 0.1% and about 5% by weight of a use solution of the pesticide composition.

The pesticide composition may also optionally include humectants such as glycerol to slow evaporation and maintain wetness of the pesticide composition after application. When a humectant is included in the pesticide composition, the humectant may constitute between about 0.5% and about 10% by weight of the pesticide composition.

The pesticide composition may also optionally include a foaming agent. When a foaming agent is included in the pesticide composition, the foaming agent may constitute between about 1% and about 10% by weight of the pesticide composition.

Packaging

The pesticide composition may be packaged by any conventional means known in the art. For example, solid form sodium lauryl sulfate and other functional ingredients may be premixed and packaged as a concentrate in a bucket. Alternatively, the pesticide composition may be packaged in a water-soluble sachet for easy disposal after use and reduced packaging waste.

Methods of Use

In general, a pesticide composition of the present invention using a solid form of sodium lauryl sulfate can be created by combining a solid form of sodium lauryl sulfate, water, and any additional functional components and allowing the components to interact. In a first embodiment, the pesticide composition may include needle form sodium lauryl sulfate and water. In an exemplary embodiment, a use solution of the pesticide composition includes between about 1% and about 10% by weight of a solid form of sodium lauryl sulfate and balance water.

In a second embodiment, the pesticide composition may include a solid form of sodium lauryl sulfate, water, attractant, humectant and foaming agent. In an exemplary embodiment, a use solution of the pesticide composition includes between about 1% and about 10% by weight active solid form sodium lauryl sulfate, between about 0.1% and about 5% by weight attractant, between about 0.5% and about 10% by weight humectant, between about 1% and about 10% by weight foaming agent and balance water.

The concentrate may be diluted with water at the location of use to provide the use solution. Once the pesticide composition has been thoroughly mixed to form a substantially homogeneous solution, the pesticide composition may be applied onto a surface as a spray or foam. The use solution is applied onto the surface for an amount of time sufficient to terminate the pests. The pesticide composition can be applied in and around areas such as apartment buildings, bakeries, beverage plants, bottling facilities, breweries, cafeterias, candy plants, canneries, cereal processing and manufacturing plants, cruise ships, dairy barns, poultry facilities, flour mills, food processing plants, frozen food plants, homes hospitals, hotels, houses, industrial buildings, kennels, kitchens, laboratories, manufacturing facilities, mausoleums, meat processing and packaging plants, meat and vegetable canneries, motels, nursing homes, office buildings, organic facilities, restaurants, schools, stores, supermarkets, warehouses and other public buildings and similar structures. In particular, the pesticide composition can be applied to surfaces, such as floors, where pests may harbor, including cracks, crevices, niches, dark areas, drains, and other harborage sites.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Panel Exposure Test 6 inch by 6 inch stainless steel panels were sprayed with a test sample. Ten adult male cockroaches were placed onto the wet panels for about 1 minute. A 6 inch diameter greased PLEXIGLASS® ring was used to ensure that the insects remained on the panel for the desired amount of time. Once the cockroaches were removed, the cockroaches were transferred to pre-greased jars for observation of mortality data. During the data collection period, the cockroaches were provided with food and water. Mortality was tracked at 1, 2, 4, 24 and 48 hours post-exposure. This test was performed 6 times.

Examples 1, 2 and 3 and Comparative Examples A, B and C

The compositions of Examples 1, 2 and 3 are compositions of the present invention using needle form sodium lauryl sulfate (SLS) as the active ingredient in a pesticide composition. The compositions of Examples 1, 2 and 3 were mixed with water to form, respectively, about 1 wt %, about 3 wt % and about 6 wt % solutions. To obtain the 3 wt % and 6 wt % solutions, heat was applied to the SLS and water combination until the SLS went into solution. The heat was applied using a microwave.

The compositions of Examples A, B and C are comparative compositions of the present invention using powder form SLS combined with water to form, respectively, about 1 wt %, about 3 wt % and about 6 wt % solutions. The compositions of Comparative D, E and F are comparative compositions using liquid form SLS combined with water to form, respectively, about 6 wt %, about 12 wt % and about 18 wt % solutions.

All forms of the sodium lauryl sulfate are commercially available from Stephan Company located in Northfield, Ill.

The various pesticide compositions were applied onto stainless steel panels as described in the panel exposure test method described above. For the compositions of Examples 1, 2 and 3 and Comparative Examples A, B, C and E, each of the tests was run a total of 6 times, with a total of 60 test cockroaches. For the compositions of Comparative Examples D and F, tests were performed less than 6 times and the mortality data was multiplied by the appropriate factor to obtain a comparable set of data. Table 1 provides the percent solution for the compositions of Examples 1, 2 and 3 and Comparative Examples A, B, C, D, E and F and the percent cockroach mortality after 48 hours.

TABLE 1

| | | Mortality | | | | | |
| --- | --- | --- | --- | --- | --- | --- | --- |
| | | 1 Hour | 2 Hours | 4 Hours | 24 Hours | 48 Hours | % mortality at 48 hours |
| Example 1 | Needle Form 1% | 1/60 | 1/60 | 1/60 | 1/60 | 5/60 | 8.33% |
| Example 2 | Needle Form 3% | 6/60 | 6/60 | 6/60 | 6/60 | 6/60 | 10% |
| Example 3 | Needle Form 6% | 15/60 | 15/60 | 15/60 | 16/60 | 18/60 | 30% |
| Comp. Ex. A | Powder Form 1% | 0/60 | 0/60 | 0/60 | 0/60 | 1/60 | 1.67% |
| Comp. Ex. B | Powder Form 3% | 5/60 | 5/60 | 5/60 | 5/60 | 7/60 | 11.67% |
| Comp. Ex. C | Powder Form 6% | 5/60 | 3/60 | 3/60 | 4/60 | 4/60 | 6.67% |
| Comp. Ex. D | Liquid Form 6% | 0/30 (0/60) | 0/30 (0/60) | 0/30 (0/60) | 1/30 (2/60) | 3/30 (6/60) | 10% |
| Comp. Ex. E | Liquid Form 12% | 0/60 | 0/60 | 0/60 | 0/60 | 1/60 | 1.67% |
| Comp. Ex. F | Liquid Form 18% | 1/30 (2/60) | 1/30 (2/60) | 1/30 (2/60) | 1/30 (2/60) | 1/30 (2/60) | 3.33% |

As illustrated in Table 1, the needle form SLS in the compositions of Examples 1, 2 and 3 resulted in generally higher rates of mortality than the powder form SLS in the compositions of Comparative Examples A, B and C and the liquid form SLS in the compositions of Comparative Examples D, E and F. In particular, with a 1% solution, the composition of Example 1 killed about 6.67% of the cockroaches over 48 hours while the composition of Comparative Example A killed about 1.67% of the cockroach over the same period of time. With a 3% solution, the composition of Example 2 killed about 10% of the cockroaches over 48 hours while the composition of Comparative Example B killed about 11.67% of the cockroaches over the same period of time. With a 6% solution, the composition of Example 3 killed about 30% of the cockroaches over 48 hours. By comparison, the compositions of Comparative Example C and Comparative Example D killed about 6.67% and about 10% of the cockroaches, respectively, over the same period of time.

Because needle form and powder form SLS would not go into solution at 12% and 18%, only liquid SLS was tested. Even with a 12% solution and 18% solution, the compositions of Comparative Example E killed only 1 cockroach and Comparative Example F only killed 2 cockroaches. Thus, the mortality rate of a 12% and 18% solution of liquid SLS was lower than the mortality rate of a 1% solution of the needle form SLS.

The only difference in the compositions of Examples 1, 2 and 3, the compositions of Comparative Examples A, B and C and the compositions of Comparative Examples D, E and F was the form of SLS used. The results in Table 1 thus illustrates that compositions including needle form SLS and powder form SLS were the more effective in killing cockroaches than compositions including liquid form SLS.

Examples 4, 5, 6, 7, 8, 9, 10, 11 and 12

After determining that needle form SLS was more efficient at killing cockroaches than either liquid form or powder form SLS, testing on the method of application of the SLS was performed. This included the amount of SLS applied onto the panels. The compositions of Examples 4, 5, 6, 7, 8, 9, 10, 11 and 12 are compositions of the present invention using needle form sodium lauryl sulfate (SLS) as the active ingredient in a pesticide composition. Each of Examples 4, 5, 6, 7, 8, 9, 10, 11 and 12 were mixed with water to form 1% solutions and applied onto the panels as described above. Example 4 applied about 0.74 grams of the pesticide composition, Example 5 applied about 0.89 grams of the pesticide composition, Example 6 applied about 1.12 grams of the pesticide composition, Example 7 applied about 1.55 grams of the pesticide composition, Example 8 applied about 2.11 grams of the pesticide composition, Example 9 applied about 2.12 grams of the pesticide composition, Example 10 applied about 2.65 grams of the pesticide composition, Example 11 applied about 2.92 grams of the pesticide composition and Example 12 applied about 4.92 grams of the pesticide composition.

Table 2 provides the grams of pesticide composition applied for Examples 4, 5, 6, 7, 8, 9, 10, 11 and 12 and the percent cockroach mortality after 48 hours.

As illustrated in Table 2, as the amount of needle form SLS applied onto the panels increased, the rate of cockroach mortality also increased. When the amount of needle form SLS applied onto the panels nearly doubled from about 0.74 grams (Example 4) to about 1.55 grams (Example 7), the percent mortality of cockroaches at 48 hours increased by about 85.42%. When the amount of needle form SLS applied onto the panels nearly doubled again from about 1.55 grams (Example 7) to about 2.92 grams (Example 11), the percent mortality of cockroaches at 48 hours increased by another about 36.84%. When the amount of needle form SLS applied onto the panels nearly doubled again from about 2.92 grams (Example 11) to about 4.92 grams (Example 12), the percent mortality of cockroaches at 48 hours increased by another about 1.3%. In all, as the amount of needle form SLS applied onto the panels increased from about 0.74 grams (Example 4) to about 4.92 grams (Example 12), the percent mortality of cockroaches at 48 hours increased by over 90%, from 8.75% to 96.25%.

Table 2 thus shows that the efficacy of sodium lauryl sulfate, and particularly needle form SLS, is related to the amount of SLS applied onto the surface of the panel.

Jar Exposure Test

The test samples were sprayed directly onto ten cockroaches that were placed into greased, 16 ounce jars. The jars were agitated to ensure that all of the cockroaches in the jar came into contact with the test sample. The cockroaches stayed in the treated jars for observation of mortality data. During the data collection period, the cockroaches were provided with food and water. Mortality was tracked at 1, 2, 4, 24 and 48 hours post-exposure. This test was performed 6 times. Generally, a cockroach mortality of about 70% or higher is considered acceptable. A cockroach mortality of about 90% or higher is considered excellent.

Examples 13, 14 and 15 and Comparative Examples G, H, I, J, K, L and M

The compositions of Examples 13, 14 and 15 are compositions of the present invention using needle form sodium lauryl sulfate (SLS) as the active ingredient in a pesticide composition. The compositions were mixed with water to form about 1 wt %, about 3 wt % and about 6 wt % solutions, respectively.

The compositions of Comparative Examples G, H and I are comparative compositions of the present invention using powder form SLS. The compositions were mixed with water to form about 1 wt %, about 3 wt % and about 6 wt % solutions, respectively. The compositions of Comparative Examples J, K, L and M are also comparative compositions using liquid form SLS. The compositions were mixed with water to form about 6 wt %, about 12 wt % and about 18 wt % solutions, respectively.

TABLE 2

| | | Mortality | | | | | |
| --- | --- | --- | --- | --- | --- | --- | --- |
| | | 1 Hour | 2 Hours | 4 Hours | 24 Hours | 48 Hours | % mortality at 48 hours |
| Example 4 | 0.74 grams | 5/80 | 7/80 | 6/80 | 7/80 | 7/80 | 8.75 |
| Example 5 | 0.89 grams | 66/80 | 69/80 | 74/80 | 67/80 | 67/80 | 83.75 |
| Example 6 | 1.12 grams | 29/80 | 28/80 | 33/80 | 30/80 | 31/80 | 38.75 |
| Example 7 | 1.55 grams | 48/80 | 48/80 | 46/80 | 48/80 | 48/80 | 60.00 |
| Example 8 | 2.11 grams | 70/80 | 71/80 | 69/80 | 67/80 | 68/80 | 85.00 |
| Example 9 | 2.12 grams | 64/80 | 69/80 | 59/80 | 62/80 | 62/80 | 77.5 |
| Example 10 | 2.65 grams | 62/80 | 64/80 | 69/80 | 67/80 | 67/80 | 83.75 |
| Example 11 | 2.92 grams | 77/80 | 78/80 | 76/80 | 76/80 | 76/80 | 95.00 |
| Example 12 | 4.92 grams | 77/80 | 77/80 | 76/80 | 77/80 | 77/80 | 96.25 |

The various exemplary compositions were sprayed into jars as described in the test method above. For the compositions of Examples 13, 14, and 15 and Comparative Examples G, H, I and J, each of the tests were run a total of 6 times, with a total of 60 test cockroaches. For the compositions of Comparative Examples K, L and M, tests were performed less than 6 times and the mortality data was multiplied by the appropriate factor to obtain a comparable set of data. Table 3 provides the percent solution for the compositions of Examples 13, 14 and 15 and the compositions of Comparative Examples G, H, I, J, K, L and M and the percent of cockroach mortality after 48 hours.

The only difference among the compositions of Examples 13, 14 and 15, the compositions of Comparative Examples G, H and I and the compositions of Comparative Examples J, K, L and M was the form of SLS used. The results in Table 3 illustrate that compositions including needle form SLS were more effective in killing cockroaches than compositions including powder and liquid form SLS. Pesticide compositions including solid form SLS may be effective at killing cockroaches, but would need to be applied at higher concentrations than pesticide compositions including powder form SLS.

TABLE 3

|  |  | Mortality | | | | | % mortality at 48 hours |
|---|---|---|---|---|---|---|---|
|  |  | 1 Hour | 2 Hours | 4 Hours | 24 Hours | 48 Hours |  |
| Example 13 | Needle Form 1% | 53/60 | 53/60 | 53/60 | 53/60 | 55/60 | 91.7% |
| Example 14 | Needle Form 3% | 52/60 | 52/60 | 52/60 | 53/60 | 53/60 | 88.33% |
| Example 15 | Needle Form 6% | 53/60 | 53/60 | 53/60 | 53/60 | 56/60 | 93.33% |
| Comp. Ex. G | Powder Form 1% | 6/60 | 7/60 | 6/60 | 7/60 | 7/60 | 11.67% |
| Comp. Ex. H | Powder Form 3% | 28/60 | 27/60 | 27/60 | 25/60 | 28/60 | 46.67% |
| Comp. Ex. I | Powder Form 6% | 26/60 | 27/60 | 26/60 | 27/60 | 32/60 | 53.33% |
| Comp. Ex. J | Liquid Form 1% | 3/10 (18/60) | 4/10 (24/60) | 4/10 (24/60) | 4/10 (24/60) | 8/10 (48/60) | 80% |
| Comp. Ex. K | Liquid Form 6% | 12/30 (24/60) | 11/30 (22/60) | 10/30 (20/60) | 9/30 (18/60) | 10/30 (20/60) | 33.33% |
| Comp. Ex. L | Liquid Form 12% | 30/60 | 25/60 | 31/60 | 31/60 | 33/60 | 55% |
| Comp. Ex. M | Liquid Form 18% | 12/20 (36/60) | 11/20 (33/60) | 11/20 (33/60) | 11/20 (33/60) | 12/20 (36/60) | 60% |

As illustrated in Table 3, the needle form SLS in the compositions of Examples 13, 14 and 15 resulted in higher rates of mortality than the powder form SLS in the compositions of Comparative Examples G, H and I and the liquid form SLS in the compositions of Comparative Examples J, K, L and M. In particular, with a 1% solution, the composition of Example 13 killed about 91.7% of the cockroaches over 48 hours while the compositions of Comparative Example G and Comparative Example J killed about 11.67% and about 80% of the cockroaches, respectively, over the same period of time. With a 3% solution, the composition of Example 14 killed about 88.33% of the cockroaches over 48 hours while the composition of Comparative Example H killed about 46.67% of the cockroaches over the same period of time. With a 6% solution, the composition of Example 15 killed about 93.33% of the cockroaches over 48 hours. By comparison, the compositions of Comparative Example I and Comparative Example K killed about 53.33% and about 33.33% of the cockroaches, respectively, over the same period of time.

Because needle form and powder form SLS would not go into solution at 12% and 18%, only the liquid SLS was tested. Even with a 12% solution and 18% solution, the compositions of Comparatives Example L and M only killed about 55% and about 60% of the cockroaches, respectively. Thus, the mortality rate of 12% and 18% solutions including liquid SLS was lower than the mortality rate of a 1% solution including needle form SLS.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention The following is claimed:

1. An aqueous pesticide composition comprising:
   (a) about 3% to 10% active solid needle form sodium lauryl sulfate by weight of the aqueous pesticide composition;
   (b) water;
   (c) at least one of about 0.1% to about 5% food attractant or pheromone by weight of the aqueous pesticide composition; about 0.5% to about 10% humectant by weight of the aqueous pesticide composition; or about 1% to about 10% foaming agent by weight of the aqueous pesticide composition, wherein the aqueous pesticide composition is effective against crawling pests.

2. The aqueous pesticide composition of claim 1, wherein the aqueous pesticide composition comprises a food attractant or a pheromone.

3. The aqueous pesticide composition of claim 1, consisting essentially of:
about 3% to about 10% active solid needle form sodium lauryl sulfate by weight of the aqueous pesticide composition;
about 0.1% to about 5% food attractant by weight of the aqueous pesticide composition; and
water.

4. The aqueous pesticide composition of claim 1, consisting essentially of:
about 3% to about 10% active solid needle form sodium lauryl sulfate by weight of the aqueous pesticide composition;
about 0.1% to about 5% food attractant by weight of the aqueous pesticide composition;
about 0.5% to about 10% humectant by weight of the aqueous pesticide composition; and
water.

5. The aqueous pesticide composition of claim 1, consisting essentially of:
about 3% to about 10% active solid needle form sodium lauryl sulfate by weight of the aqueous pesticide composition;
about 0.1% to about 5% food attractant by weight of the aqueous pesticide composition;
about 1% to about 10% foaming agent by weight of the aqueous pesticide composition; and
water.

6. The aqueous pesticide composition of claim 1, consisting essentially of:
about 3% to about 10% active solid needle form sodium lauryl sulfate by weight of the aqueous pesticide composition;
about 0.1% to about 5% food attractant by weight of the aqueous pesticide composition;
about 0.5% to about 10% humectant by weight of the aqueous pesticide composition;
about 1% to about 10% foaming agent by weight of the aqueous pesticide composition; and
water.

7. The aqueous pesticide composition of claim 1, consisting essentially of:
about 3% to about 10% active solid needle form sodium lauryl sulfate by weight of the aqueous pesticide composition;
about 0.5% to about 10% humectant by weight of the aqueous pesticide composition; and
water.

8. The aqueous pesticide composition of claim 1, consisting essentially of:
about 3% to about 10% active solid needle form sodium lauryl sulfate by weight of the aqueous pesticide composition;
about 0.5% to about 10% humectant by weight of the aqueous pesticide composition;
about 1% to about 10% foaming agent by weight of the aqueous pesticide composition; and
water.

9. The aqueous pesticide composition of claim 1, consisting essentially of:
about 3% to about 10% active solid needle form sodium lauryl sulfate by weight of the aqueous pesticide composition;
about 1% to about 10% foaming agent by weight of the aqueous pesticide composition; and
water.

10. The aqueous pesticide composition of claim 1, wherein the aqueous pesticide composition contains about 3% to 6% active solid needle form sodium lauryl sulfate by weight.

11. An aqueous pesticide composition for eliminating crawling pests, comprising water and a pesticide component, wherein the pesticide component comprises solid needle form sodium lauryl sulfate dissolved in the water, wherein the aqueous pesticide composition for eliminating crawling pests is free of pesticides that are not considered minimum risk pesticides, and the aqueous pesticide composition contains from about 3% to 10% by weight of the pesticide component; and
about 0.1% to about 5% of an attractant, about 0.5% to about 10% of a humectant, about 1% to about 10% of a foaming agent, or a combination thereof.

12. The aqueous pesticide composition of claim 11, wherein the attractant comprises a food attractant or a pheromone.

13. The aqueous pesticides composition of claim 11, wherein the aqueous pesticide component comprises about 3% to about 6% of the aqueous pesticide composition by weight.

14. The aqueous pesticide composition of claim 2, wherein the aqueous pesticide composition comprises a cockroach pheromone.

15. The aqueous pesticide composition of claim 1, wherein the aqueous pesticide composition is effective against cockroaches.

16. The aqueous pesticide composition of claim 1, wherein the aqueous pesticide composition is free of components that are toxic or carcinogenic to humans.

17. The aqueous pesticide composition of claim 11, wherein the pesticide component is sodium lauryl sulfate.

* * * * *

UNITED STATES PATENT AND TRADEMARK OFFICE
CERTIFICATE OF CORRECTION

PATENT NO. : 9,675,068 B2
APPLICATION NO. : 14/569439
DATED : June 13, 2017
INVENTOR(S) : Herrera et al.

It is certified that error appears in the above-identified patent and that said Letters Patent is hereby corrected as shown below:

In the Claims

Column 12, Line 40, Claim 13: "The aqueous pesticides composition" should read --The aqueous pesticide composition--

Signed and Sealed this
Fourteenth Day of April, 2020

Andrei Iancu
*Director of the United States Patent and Trademark Office*